United States Patent
Park et al.

(10) Patent No.: US 10,837,010 B2
(45) Date of Patent: Nov. 17, 2020

(54) POROUS SOLID PHASE FOR RAPIDLY ISOLATING BIOLOGICAL MOLECULES FOR NUCLEIC ACID AMPLIFICATION REACTION FROM BIOLOGICAL SAMPLE, AND USE THEREOF

(71) Applicant: BIO CUBE SYSTEM CO., LTD., Hwaseong-si (KR)

(72) Inventors: Daeho Park, Yongin-si (KR); Junsung Shin, Goyang-si (KR); Jung-Heon Han, Anyang-si (KR); Guem Suk In, Siheung-si (KR); Jeong Soo Kim, Andong-si (KR)

(73) Assignee: BIO CUBE SYSTEM CO., LTD., Hwaseong-si (KR)

(*) Notice: Subject to any disclaimer, the term of this patent is extended or adjusted under 35 U.S.C. 154(b) by 103 days.

(21) Appl. No.: 15/933,394

(22) Filed: Mar. 23, 2018

(65) Prior Publication Data

US 2018/0282717 A1    Oct. 4, 2018

Related U.S. Application Data

(62) Division of application No. 14/423,135, filed as application No. PCT/KR2013/007469 on Aug. 20, 2013, now abandoned.

(30) Foreign Application Priority Data

Aug. 28, 2012 (KR) .................. 10-2012-0094046

(51) Int. Cl.
*C12Q 1/68* (2018.01)
*C12N 15/10* (2006.01)
(Continued)

(52) U.S. Cl.
CPC ............ *C12N 15/1006* (2013.01); *C01F 7/02* (2013.01); *C01G 9/02* (2013.01); *C01G 21/06* (2013.01);
(Continued)

(58) Field of Classification Search
None
See application file for complete search history.

(56) References Cited

U.S. PATENT DOCUMENTS

2004/0161741 A1    8/2004    Rabani et al.
2005/0176588 A1    8/2005    Bulow
(Continued)

FOREIGN PATENT DOCUMENTS

EP    1870462 A1    12/2007
EP    1964920 A1    9/2008
(Continued)

OTHER PUBLICATIONS

Chen et al. (Journal of Magnetism and Magnetic Materials, 2010, vol. 322, p. 2439-2445). (Year: 2010).*

(Continued)

*Primary Examiner* — Stephanie K Mummert
(74) *Attorney, Agent, or Firm* — Revolution IP, PLLC (57) ABSTRACT

A method for rapidly isolating a biological molecule for a nucleic acid amplification reaction from a biological sample, the method comprising: putting a cubical shaped-porous solid phase having a plurality of pores varied in size in contact with a biological sample to get the biological molecule present in the biological sample sucked into pores of the cubical shaped-porous solid phase, wherein the cubical shaped-porous solid phase is made of ceramic having oxide material, which is selected from the group consisting of Al2O3, Fe2O3, low temperature co-fired ceramic (LTCC), PbO, and ZnO.

4 Claims, 8 Drawing Sheets (51) Int. Cl.
*C12Q 1/6806* (2018.01)
*C01F 7/02* (2006.01)
*C01G 9/02* (2006.01)
*C01G 21/06* (2006.01)
*C01G 49/06* (2006.01)
*C12Q 1/686* (2018.01)

(52) U.S. Cl.
CPC ............. *C01G 49/06* (2013.01); *C12Q 1/686* (2013.01); *C12Q 1/6806* (2013.01)

(56) References Cited

U.S. PATENT DOCUMENTS

| | | |
|---|---|---|
| 2006/0263799 A1 | 11/2006 | Dertinger et al. |
| 2007/0148649 A1 | 6/2007 | Shigesada et al. |
| 2007/0181482 A1 | 8/2007 | Abudokirim et al. |
| 2008/0026451 A1 | 1/2008 | Braman et al. |
| 2008/0033161 A1 | 2/2008 | Kanehara |
| 2008/0213564 A1* | 9/2008 | Ma ............................ C08J 9/36 428/304.4 |
| 2009/0186345 A1 | 7/2009 | Yamashita et al. |
| 2010/0234238 A1 | 9/2010 | Versele et al. |
| 2011/0015379 A1 | 1/2011 | Mori et al. |

FOREIGN PATENT DOCUMENTS

| | | |
|---|---|---|
| EP | 2218791 A1 | 8/2010 |
| JP | 10-257887 A | 9/1998 |
| JP | 2004-201607 A | 7/2004 |
| JP | 2006-223309 A | 8/2006 |
| JP | 2009-112317 A | 5/2009 |
| JP | 2009-540868 A | 11/2009 |
| JP | 2010-507384 A | 3/2010 |
| JP | 2010-094136 A | 4/2010 |
| JP | 2010-233579 A | 10/2010 |
| KR | 10-2006-0093063 A | 8/2006 |
| WO | 01/14590 A2 | 3/2001 |
| WO | 2005/078088 A1 | 8/2005 |
| WO | WO-2012145574 A2 * | 10/2012 ........... C12Q 1/6837 |

OTHER PUBLICATIONS

Huber et al. (Eur Phys J Special Topics, 2007, 141, p. 101-105) (Year: 2007).*
International Search Report for PCT/KR2013/007469 dated Dec. 23, 2013 from Korean Intellectual Property Office.
Lee, Jin-Hyeong et al., "Super high speed/high efficiency Organic Molecule Separation Technology using Magnetic-meso porous Ceramic Material", Ceramist, 2009, vol. 12, No. 6, pp. 21-28.
Brian J Taylor et al., "Real-time PCR detection of Plasmodium directly from whole blood and filter paper samples", Malaria Journal, Aug. 19, 2011, 10:244, pp. 2-8.
Jitae Kim et al., "A PCR reactor with an integrated alumina membrane for nucleic acid isolation", The Analyst, vol. 135, No. 9, Jan. 1, 2010, pp. 2408-2414.
Dafeng Chen et al., "An integrated, self-contained microfluidic cassette for isolation, amplification, and detection of nucleic acids", Biomedical Microdevices, Kluwer Academic Publishers, BO, vol. 12, No. 4, Apr. 17, 2010, pp. 705-719.

* cited by examiner

POROUS SOLID PHASE FOR RAPIDLY ISOLATING BIOLOGICAL MOLECULES FOR NUCLEIC ACID AMPLIFICATION REACTION FROM BIOLOGICAL SAMPLE, AND USE THEREOF

CROSS REFERENCE TO PRIOR APPLICATIONS

This application is a Division of U.S. patent application Ser. No. 14/423,135 filed on Feb. 23, 2015, which is a National Stage Application of PCT International Patent Application No. PCT/KR2013/007469 filed on Aug. 20, 2013, under 35 U.S.C. § 371, which claims priority to Korean Patent Application No. 10-2012-0094046 filed on Aug. 28, 2012, which are all hereby incorporated by reference in their entirety.

BACKGROUND

The present invention relates to a porous solid phase for rapidly isolating biological molecules for a nucleic acid amplification reaction from a biological sample, and a use thereof. More specifically, the present invention relates to a method for rapidly isolating biological molecules for a nucleic acid amplification reaction from a biological sample including putting a porous solid phase in contact with a biological sample to get biological molecules present in the biological sample sucked into the pores of the porous solid phase; a method for amplifying a target sequence in a biological sample including directly adding a porous solid phase, into the pores of which biological molecules present in a biological sample are sucked by putting the porous solid phase in contact with the biological sample, or performing a reverse transcriptase reaction followed by amplifying a target sequence using the porous solid phase as a template for a nucleic acid amplification reaction; a method for rapidly determining the presence of the target sequence in the biological sample using the method; and a kit and a composition for rapidly isolating biological molecules for a nucleic acid amplification reaction from a biological sample including a porous solid phase capable of rapidly sucking biological molecules present in the biological sample into the pores.

Among the methods for detecting pathogens causing diseases in animals and plants, most widely used are the serological diagnosis method for detecting intrinsic proteins of pathogens and the molecular biological diagnosis method for detecting nucleic acids. The most widely used molecular biological diagnosis method is a polymerase chain reaction (PCR), which has high detection sensitivity and can be easily used by any one. For performing PCR, it is a prerequisite to extract a genetic material to be used as a template from a subject tissue. Currently available methods of DNA extraction are a method of using phenol/chloroform, a salting-out extraction, a method using chaotropic salt and silica resin, a method of using affinity resin, an ion exchange chromatography, and a method using magnetic beads, etc. These methods are described in U.S. Pat. Nos. 5,057,426 and 4,923,978, EP Patent Nos. 0512767 A1 and 0515484B, WO 95/13368, WO 97/10331, and WO 96/18731, etc. These describe methods of isolating nucleic acids after binding the nucleic acids to a solid support phase. The previously used methods employ a certain kind of solvents in order to isolate nucleic acids.

The amplification of a target area from DNA or RNA template via PCR can be used in various fields such as DNA molecule labeling, manufacturing probes, construction of cDNA and genomic DNA libraries, inspection of pathogens, etc. For example, when a genetic material of a pathogen is amplified, the presence of the pathogen in a specimen can be easily diagnosed based on the presence/absence of the amplified target product. In the case when PCR is used for the diagnosis of pathogens, it may have a difficulty in examining a large amount of a sample at one trial although PCR has high specificity and detection sensitivity. This is because the rapid separation of a PCR template from various specimens requires a considerable amount of time and costs. Numerous methods for isolating DNA or RNA from various tissues have been reported, and other methods to easily obtain a genetic material available for PCR such as a method of boiling blood, hairs, epithelial cells, leaf slices, NaOH treatment, virion capture, heat extraction, microwave extraction, NaOH extraction, etc., have been also reported. However, these methods have drawbacks that the extraction efficiency of the genetic material is not uniform, and reproducibility of PCR reaction is low. Accordingly, it can be easily assumed that if biological molecules to be used as a template for PCR can be easily extracted in large amounts from various subjects without damaging the high specificity and detection sensitivity of PCR technology, the utilization of PCR will be much higher than now.

Meanwhile, KR Patent Publication No. 2005-0088164 discloses a method of nucleic acid isolation, and JP Patent Publication No. 2007-506404 discloses a method for rapid detection of nucleic acid molecules. However, there has been no report on the method of rapidly isolating biological molecules for a nucleic acid amplification reaction from a biological sample by using a porous solid phase as in the present invention.

SUMMARY

The present invention being drawn by the above request, the present inventors placed a porous ceramic cube of an oxide material, which is a porous solid phase, to be in contact with a cucumber mosaic virus (CMV)-infected pepper leaf as a biological sample by pressing with a flat portion on the rear side of metal tweezers and RNA, gDNA and viral particles present in the pepper sample are sucked into the pores of the porous ceramic cube, the porous ceramic cube keeping the materials was directly added into a PCR tube as a template without a solvent extraction process using an additional solvent regarding the sucked biological molecules, and amplified using a CMV-specific primer, and confirmed that it was a CMV-infected pepper. The above method was applied to purified CMV particles, CMV-infected total RNA, and purified genomic DNA of pepper, and found that the genetic materials could be efficiently obtained according to the material of the ceramic cube and the manufacturing temperature, thus being usable in PCR and cDNA synthesis. Additionally, a multiplex RT-PCR using the nucleic acid isolated from tobacco leaves by the LTCC cube of the present invention as a template and BAC plasmid amplification regarding *E. coli* were successfully carried out.

Accordingly, the present invention was completed by confirming that it enables a rapid diagnosis of the presence of a target sequence via a rapid isolation of biological molecules present in a biological sample.

In order to solve the problem, the present provides a method for rapidly isolating biological molecules for a nucleic acid amplification reaction from a biological sample including putting a porous solid phase in contact with a biological sample, in which biological molecules of interest are sucked into the pores of the porous solid phase.

Further, the present provides a method for amplifying a target sequence in a biological sample including directly adding a porous solid phase, into the pores of which biological molecules present in a biological sample are sucked by putting the porous solid phase in contact with the biological sample, or performing a reverse transcriptase reaction for cDNA synthesis followed by amplifying a target sequence using the porous solid phase as a template for a nucleic acid amplification reaction, and a method for rapidly determining the presence of the target sequence in the biological sample using the method.

Additionally, the present invention also provides a kit for a nucleic acid amplification reaction for amplifying a target sequence in a biological sample including a porous solid phase capable of rapidly sucking biological molecules present in the biological sample into the pores of the porous solid phase.

Additionally, the present invention provides a kit and a composition for rapidly isolating biological molecules for a nucleic acid amplification reaction from a biological sample including a porous solid phase capable of rapidly sucking biological molecules present in the biological sample into the pores of the porous solid phase.

The present invention enables a rapid diagnosis of the presence of a target sequence via rapid isolation of biological molecules present in a biological sample and thus can be easily used for rapid and accurate determination of amplification of target genome DNA, cDNA synthesis, the presence of pathogenic inflammation, etc.

BRIEF DESCRIPTION OF THE DRAWINGS

FIG. 1 is a diagram illustrating the adsorption of a genetic material using a porous ceramic cube and its utilization as a RT-PCR/PCR template, wherein A is a porous ceramic cube; B is an enlarged picture of the porous ceramic cube wherein 14 kinds of cubes are prepared by varying materials and manufacturing temperature so that the size of pores on the surface of the 1 $mm^3$ cubes become varied accordingly; C shows a design wherein when a single cube is placed on a plant leaf and pressed with the a flat portion on the rear side of metal tweezers thereon, the leaf tissues are destroyed and simultaneously the genetic material is sucked into the pores of the cube; D shows the use of a single genetic material-absorbed cube used as a template for RT-PCR or PCR; and E shows that the thus obtained PCR product is confirmed on an agarose gel.

FIG. 2 shows results of separating DNA/RNA templates for a nucleic acid amplification from a biological sample using cut-out fragments of a ceramic pot, wherein A shows cut-out ceramic fragments (1-8) used for the preparation of a ceramic fragment with a size of about 1 $mm^3$, wherein 6 refers to the arrow region of the cut-out ceramic fragment 5; B shows the results of PCR reaction performed using 8 kinds of ceramic fragments, being placed on the *Capsicum annuum* CM334 pepper leaf and pressed by a flat portion on the rear side of metal tweezers, as a template along with a Tscar primer; C shows the results of PCR reaction performed using gDNA (1 μg/μL), purified from CM334 pepper leaf being sucked into 8 kinds of ceramic fragments prepared in A, as a template along with a Tscar primer, wherein lane M indicates a 1 kb DNA ladder, and lane PC indicates the result when 1 μL of gDNA (1 μg/μL) purified from the CM334 pepper leaf was used as a template for PCR; and D shows the result of Tomato spotted wilt virus (TSWV) detection by RT-PCR, wherein lane M indicates a 1 kb DNA ladder, lane NC indicates a result wherein 1 μL of the total RNA isolated from sound *Nicotiana rustica* tobacco leaf was used as a template for reverse-transcription, lane PC indicates a result, where the total RNA isolated from the tobacco leaf artificially infected with TSWV was used as a template for reverse-transcription, wherein lanes 1-8 indicate the results of using the 8 kinds of ceramic fragments, being pressed on the TSWV-infected *N. rustica* tobacco leaf thereby sucking the biological molecules (in particular, virus particles or RNA), as a template for reverse-transcription reaction, wherein the arrows indicate the predicted size of PCR products.

FIG. 11 shows a result of the characteristics of cube surfaces on the amplification efficiency of PCR products. Pictures A-C were observed under 1000-fold magnification of SEM, wherein A indicates 33 (LTCC, 800° C.) without cube abrasion; B indicates 33 with 48 hours of abrasion; and C indicates 33 with 72 hours of abrasion. Regarding the pictures D and E: lane M indicates a 1 kb DNA ladder; lane PC is a result where 1 μL of purified gDNA was used as a template; lane 39 indicates 33 (LTCC, 800° C.) without cube abrasion; lane 41 indicates 33 with 48 hours of abrasion; and lane 42 indicates 33 with 72 hours of abrasion along with the use of primers 10(D) and 146(E).

DETAILED DESCRIPTION

In order to accomplish the object of the present invention, the present invention provides a method for rapidly isolating biological molecules for a nucleic acid amplification reaction from a biological sample including putting a porous solid phase in contact with a biological sample, in which biological molecules of interest are sucked into the pores of the porous solid phase.

In a method according to an embodiment of the present invention, the biological samples may be derived from an animal, a plant, a bacterium, or a fungus, and preferably, may be a plant or an animal, but is not limited thereto.

In the present invention, the method of putting a porous solid phase in contact with a biological sample refers to a method to induce the absorption of the biological sample into the porous solid phase via a simple contact when the type of the biological sample is a liquid phase, and to keep the biological molecules released when cells are disrupted by pressing the porous solid phase with a flat portion on the rear side of metal tweezers when the type of the biological sample is a solid phase, but is not limited thereto.

In an embodiment of the present invention, the biological molecules may be DNA, RNA, dsRNA, microRNA, viroid, virus, bacteria, fungi or microalgae, but is not limited thereto.

The biological molecules of the present invention may be obtained from various sources in the case of an animal, for example, muscles, epidermis, blood, bones, and organs, and most preferably from muscles or blood, but is not limited thereto. In the case of a plant, the biological molecules may be obtained from various organ extracts, for example, leaves, flowers, stems, roots, fruits, and seeds, and most preferably from leaves, seeds or flowers, but is not limited thereto. In the case of microorganisms, the biological molecules may be obtained from colonies, mycelia or ooze, and most preferably from the sites with a dense habitation (the areas with lesions), but is not limited thereto. In the case of virus, bacteria, fungi, or microalgae, the analysis of a target gene is possible by putting the porous solid phase, where the size of their pores are appropriately adjusted, into contact, sucking partial particles or entire cells into the pores, and performing a PCR reaction using them as a template, thereby releasing the nucleic acids therein by the tissue destruction at high temperature denaturation step (about 94° C. to 96° C.) during the PCR reaction.

The biological molecule of the present invention may also include nucleotides, which are the basic constitutional unit of nucleic acids, and its analogues with modified bases.

In the method of the present invention, when the isolated biological molecule is gDNA it may be sucked by allowing a front end of a ceramic rod to contact with the biological sample. When the starting material is mRNA a front end of a ceramic rod is allowed to contact with the biological sample, and cDNA is synthesized using the total RNA adsorbed onto the front end as a template with reverse transcriptase. Since the total RNA is the one isolated from a plant or animal cell, there is a poly-A tail at the end of the mRNA, and cDNA can be easily synthesized using an oligo dT primer and a reverse transcriptase based on the characteristics of the sequence. Additionally, in the case of a virus, when there is a poly-A tail, cDNA can be synthesized in the same manner as described above, however, when the poly-A is absent (for example, tobacco mosaic virus), cDNA can be synthesized using a target RNA-specific antisense primer according to a method known in the art.

In the method of the present invention, the above small amount of biological molecule may be applied to various methods known in the art where it can be used as a template. For example, the technologies to be applied in the present invention may include CAPS or SCAR molecular marker, HRM using a fluorescent marker, real time PCR, Nested PCR, immunocapture PCR, a multiplex PCR used for concurrently detecting various pathogens, direct determination of DNA sequences, single-stranded confirmation analysis (Orita et al., PNAS, USA 86:2776(1989)), RNase protection analysis (Finkelstein et al., Genomics, 7:167(1990)), Denaturing Gradient Gel Electrophoresis (Wartell et al., Nucl. Acids Res., 18:2699(1990)), a method using a protein capable of recognizing nucleotide mismatches (e.g., mutS protein of E. coli) (Modrich, Ann. Rev. Genet., 25:229-253 (1991)), allele-specific PCR, but is not limited thereto.

When a nucleic acid amplification technology is applied, it is important to design an appropriate primer for virus detection of the present invention. However, the amount of the template amplification can be increased when RT and PCR are performed separately in two different tubes rather than when they are performed in the same tube, thereby improving the reliability of virus verification results. According to a preferred embodiment of the present invention, there is provided a method for analyzing the presence/absence of virus within tissues using a genotyping primer designed to be matched with nucleotides sucked into the ceramic block.

The nucleic acid amplification of the present invention can be used for the manufacture of DNA molecular markers, construction of probes, construction of cDNA and genomic DNA libraries, inspection of pathogens, but is not limited thereto.

In a method according to an embodiment of the present invention, the above nucleic acid amplification reaction may be via cDNA synthesis, polymerase chain reaction (PCR), multiplex PCR, reverse transcriptase polymerase chain reaction (RT-PCR), ligase chain reaction, nucleic acid sequence-based amplification, transcription-based amplification system, strand displacement amplification or amplification using Qβ replicase, or any method suitable for amplifying nucleic acid molecules known in the art. In the above, PCR refers to a method of amplifying a target nucleic acid from a primer pair specifically binding to target nucleic acid using a polymerase. These PCR methods are well known in the art, and a commercially available kit may be also used.

In a method according to an embodiment of the present invention, the porous solid phase is at least one selected from the group consisting of carbonized cellulose, paper crumpled in a particulate form, natural or synthetic zeolite, polystyrene, polycarbonate, polyprophylene, porous metal particle, porous rubber, microporous glass held together in a particle form, lime, a shell, a ceramic fragment, or ceramic of oxide material, and preferably a ceramic of oxide material, but is not limited thereto.

In a method according to an embodiment of the present invention, the ceramic of oxide material may be a ceramic prepared using $Al_2O_3$, $Fe_2O_3$, LTCC (Low Temperature Co-fired ceramic), PbO or ZnO as main ingredients, but is not limited thereto.

In a method according to an embodiment of the present invention, the porous solid phase may be in the shape of a cube, a cuboid, a sphere, a cylinder, a bar, a bar with a dent at one end and a sharp end, or a bar with a dent at one end and a sharp end and a large pore inside the sharp end, but is not limited thereto.

When the ceramic of oxide material is used as a porous solid phase of the present invention its pore size can be adjusted. When a porous ceramic is manufactured using the same oxide material the size and number of pore can be adjusted according to the manufacturing temperature, and thus PCR or RT-PCR can be effectively performed using the optimized porous ceramic according to the type of biological molecules to be targeted. Regarding the pore size of such porous ceramic, the size of the porous solid phase may be appropriately adjusted so that it can selectively suck the targeted biological molecules. Additionally, although the external size of the above oxide material is not particularly limited if the ceramic can easily introduced into a PCR tube, for example, it may be 1 $mm^3$, but is not limited thereto.

Also, the present invention provides a method for amplifying a target sequence in a biological sample including:
(a) putting a porous solid phase in contact with a biological sample, in which biological molecules of interest are sucked into the pores of the porous solid phase; and
(b) adding the porous solid phase, into which the biological molecules in step (a) were sucked, as a template for a nucleic acid amplification reaction, and performing the amplification reaction using a target primer set, to amplify the target sequence.

In an embodiment of the present invention, the above nucleic acid amplification method is the same as described above.

Also, the present invention provides a method for amplifying a target sequence in a biological sample including:
(a) putting a porous solid phase in contact with a biological samples in which biological molecules of interest are sucked into the pores of the porous solid phase; and
(b) adding reverse transcriptase to the porous solid phase in step (a), into which the biological molecules were sucked, and performing a reverse transcriptase reaction; and
(c) adding the reverse transcriptase reaction product as a template for a nucleic acid amplification reaction, and performing an amplification reaction using a target primer set thereby amplifying the target sequence.

Also, the present invention provides a method for rapidly detecting the presence of a target sequence in a biological sample including:
(a) putting a porous solid phase in contact with a biological sample, in which biological molecules of interest are sucked into the pores of the porous solid phase;
(b) adding the porous solid phase in step (a), into which the biological molecules were sucked, as a template for a nucleic acid amplification reaction, and performing an amplification reaction using a target primer set to amplify the target sequence; and
(c) detecting the amplified product.

Also, the present invention provides a method for rapidly detecting the presence of a target sequence in a biological sample including:
(a) putting a porous solid phase in contact with a biological sample, in which biological molecules of interest are sucked into the pores of the porous solid phase;
(b) adding reverse transcriptase to the porous solid phase in step (a), into which the biological molecules were sucked, and performing a reverse transcriptase reaction;
(c) adding the reverse transcriptase reaction product as a template for a nucleic acid amplification reaction, and performing an amplification reaction using a target primer set to amplify the target sequence; and
(d) detecting the amplified product.

The method of the present invention includes detecting the amplified product. The detection of the amplified product may be performed via DNA chips, gel electrophoresis, measurement of radioactivity, measurement of fluorescence, or measurement of phosphorescence, but is not limited thereto. As a method of detecting the amplified product, gel electrophoresis may be performed. According to the size of the amplified product, the gel electrophoresis to be used may be an agarose gel electrophoresis or acrylamide gel electrophoresis. Additionally, the method of fluorescent measurement can be carried out by performing a PCR reaction after labeling the 5'-terminal with Cy-5 or Cy-3 so that a detectable target sequence is labeled as a fluorescence-labeled material and thereby the labeled fluorescence can be measured using a fluorimeter. Additionally, the method of radioactivity measurement can be carried out by adding a radioactive isotope such as $^{32}P$ or $^{35}S$ into a solution for PCR reaction when performing a PCR reaction so that the amplified product can be radiolabeled, and the radioactivity of the labeled amplified product can be measured using a radioactivity measuring device, for example, a Geiger counter or a liquid scintillation counter.

Also, the present invention provides a kit for a nucleic acid amplification reaction for amplifying a target sequence in a biological sample including a porous solid phase capable of rapidly sucking biological molecules present in the biological sample into the pores of the porous solid phase; a target primer set; and a reagent for performing an amplification reaction.

The kit for the nucleic acid amplification reaction may include reagents used for microRNA isolation, small RNA isolation, or cDNA synthesis, but is not limited thereto.

In an embodiment of the present invention, the reagent for the nucleic acid amplification reaction may include DNA polymerase, dNTPs, buffers, etc. Additionally, the kit of the present invention may further include a user guide where the optimum conditions for performing the reaction are described. The user guide is, for example, a printed product which provides explanations on a method for preparing a PCR buffer, suggested reaction conditions, etc. The user guide should include explanations in a guide book such as a pamphlet or a leaflet, a label attached to a kit, and on the surface of a package containing the kit. Additionally, the user guide should include information being provided through an electric medium such as an internet In a kit according to an embodiment of the present invention, the nucleic acid amplification reaction may be cDNA synthesis, polymerase chain reaction (PCR), multiplex PCR or reverse transcriptase polymerase chain reaction (RT-PCR), but is not limited thereto. Additionally, the porous solid phase is the same as described above.

Also, the present invention provides a kit for rapidly isolating biological molecules for a nucleic acid amplification reaction from a biological sample including a porous solid phase capable of rapidly sucking the biological molecules present in the biological sample into the pores of the porous solid phase.

In a kit according to an embodiment of the present invention, the nucleic acid amplification reaction may be cDNA synthesis, polymerase chain reaction (PCR), multiplex PCR or reverse transcriptase polymerase chain reaction (RT-PCR), but is not limited thereto. Additionally, the porous solid phase is the same as described above.

Additionally, the present invention provides a composition for rapidly isolating biological molecules for a nucleic acid amplification reaction from a biological sample including a porous solid phase capable of rapidly sucking the biological molecules present in the biological sample into the pores of the porous solid phase. The above composition includes a porous solid phase, into which biological molecules present in a biological sample of the present invention can be sucked, as an active ingredient, and by rapidly sucking the biological molecules present in a biological sample into the pores of the porous solid phase, it can be used for a nucleic acid amplification reaction. The porous solid phase is the same as described above.

In a composition according to an embodiment of the present invention, the nucleic acid amplification reaction may be cDNA synthesis, polymerase chain reaction (PCR), multiplex PCR or reverse transcriptase polymerase chain reaction (RT-PCR), but is not limited thereto. Additionally, the porous solid phase is the same as described above.

Hereinafter, the present invention will be described in more detail with reference to the following examples. However, the following examples are provided for illustrative purposes only, and the scope of the present invention should not be limited thereto in any manner.

Figure 1:
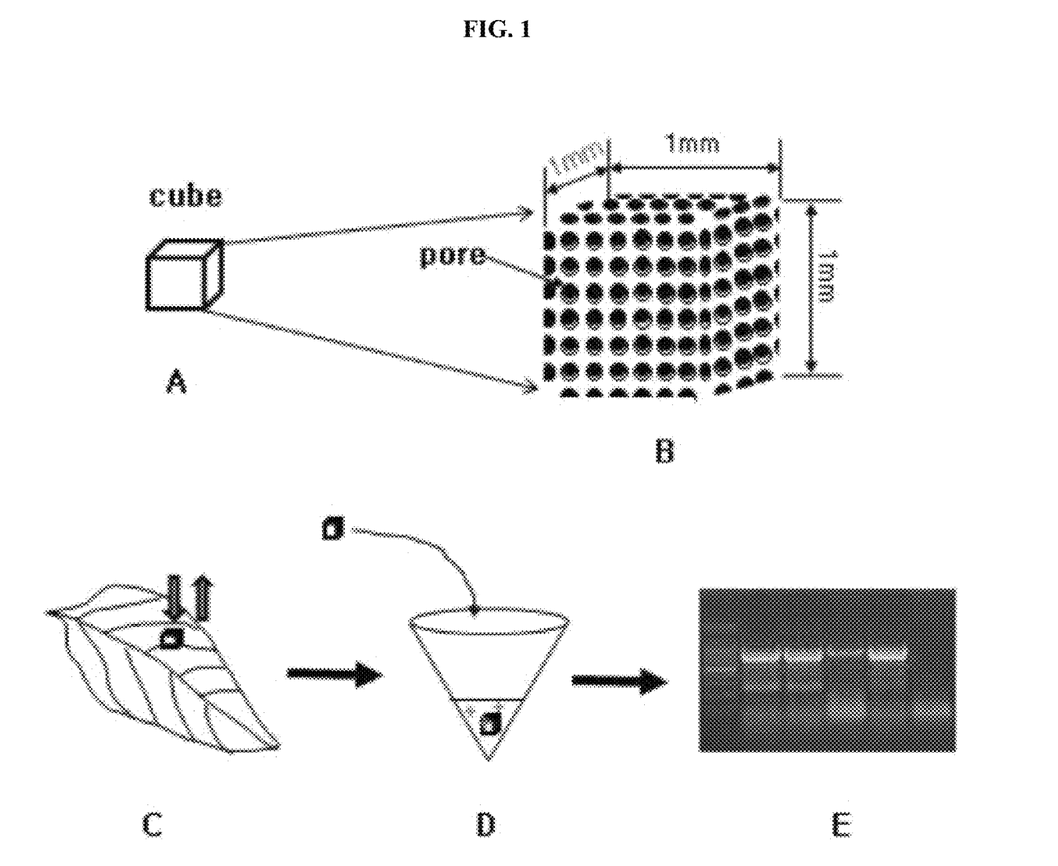

Example 1. Adsorption of a Genetic Material Using a Porous Ceramic Cube and its Use as a Template for RT-PCR/PCR The adsorption of a genetic material using a porous ceramic cube of the present invention and a diagram illustrating its use as a template for RT-PCR/PCR is shown in FIG. 1. In the present invention, 14 kinds of cubes were manufactured by varying the manufacturing temperature using the main components described in Table 1 so that the size of pores on the surface of the 1 mm$^3$ cube can vary, and the enlarged view of the porous ceramic cube is shown in FIG. 1B. Since cubes are porous smaller substances than the pores can be sucked. The present invention aims at selectively absorbing the desirable ones among various substances generated during rupture of tissues by varying the size of pores (In general, when ceramics are manufactured at high temperature the pore size becomes smaller), that is, providing a cube with an ultrafiltration function to be capable of maximally excluding PCR inhibiting substances depending on the pore size.

The present invention, a single porous ceramic cube manufactured above was placed on top of a plant leaf, and pressed with a flat portion on the rear side of metal tweezers so that the genetic substance can be simultaneously sucked into the pores of the cube while the pressed tissues are burst, and the result of using the single cube into which the genetic substance was sucked as a template for RT-PCR or PCR was confirmed in an agarose gel (FIG. 1E).

Figure 2:
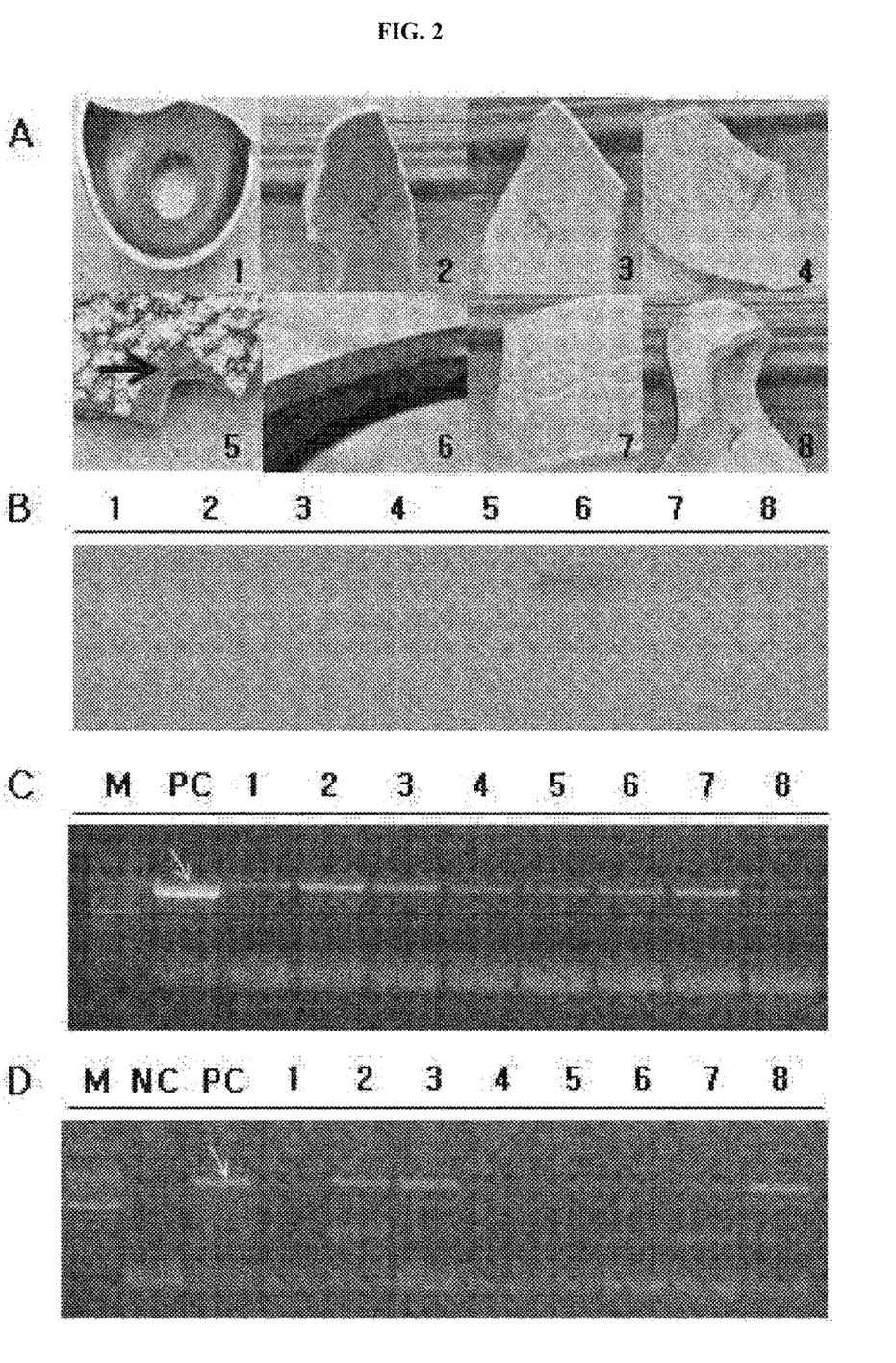

Example 2. Isolation of a DNA/RNA Template for Nucleic Acid Amplification from a Biological Sample Using a Cut-Out Ceramic Fragment Seven kinds of cut-out ceramic fragments including blue and white porcelain was broken into small pieces using a nipper, and the fragments with a volume of about 1 mm$^3$ selected from the unglazed area were used as an absorptive material for a genetic material. For the 5$^{th}$ ceramic fragment in FIG. 2A, it was divided into yellow and grey according to the area coated with glaze, and the yellow fragments and the grey fragments obtained respectively therefrom were indicated as 5 and 6, respectively. Each ceramic fragment was placed on top of *Capsicum annuum* CM334 pepper leaves, lightly pressed with a flat portion on the rear side of metal tweezers to obtain gDNA. One ceramic fragment keeping gDNA was added into each PCR tube, which was already added with a primer premix capable of verifying molecular markers related to the trichomes of pepper. The PCR premix consisted of 0.5 µL of a 10 pmol sense primer (Tsca-F: AAACGCCATCATTCGTTTTC: SEQ ID NO: 1), 0.5 µL of a 10 pmol antisense primer (Tsca-R: CATGAAAGTTGAC-CCGAACA: SEQ ID NO: 2), 4 µL of rTaq-Mix, and 15 µL of DW. The PCR product was denatured at 94° C. for 3 minutes, amplified under the set conditions (94° C./30 sec, 59° C./30 sec, 72° C./60 sec) via 35 amplification cycles, and reacted at 72° C./5 min, and the resultant was electrophoresed on a 1% agarose gel containing EtBr, and confirmed whether the target PCR product was amplified.

Figure 3:
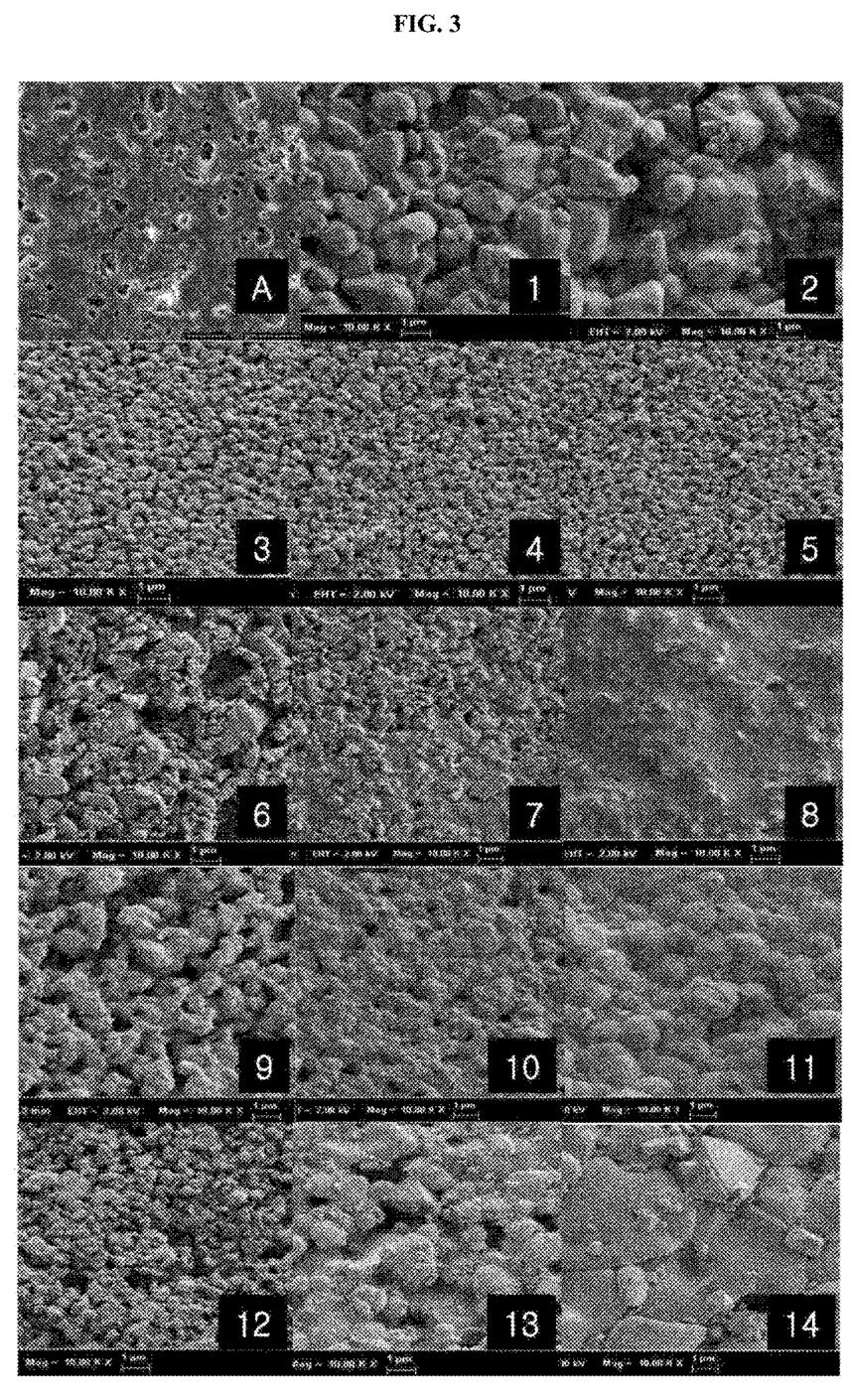
FIG. 3 shows a picture of the surface of the porous ceramic cube prepared using ceramic fragments (A) of FIG. 2A and respective oxide material with the best genome DNA amplification magnified under scanning electron microscope (SEM), wherein all the pictures were observed under 10,000-fold magnification, and the size and number of pores vary according to the materials and manufacturing temperature used therein, and the lanes 1-14 indicate the materials used as shown in Table 1 in that order and a bar of 1 μm.

As a result, as shown in FIG. 2B, the amplification of PCR products in ceramic fragments 4, 5 and 6 were confirmed. Upon examination of the surface of the ceramic fragment 4, which showed the best genomic DNA amplification, under electronic microscope, it was confirmed that the pores in the ceramics were present in various sizes (FIG. 3A). However, there was a bit of difficulty in clearly distinguishing the kinds of ceramic fragments and amplification efficiency of PCR products when the surfaces or areas of ceramic fragments were not identically controllable.

Accordingly, in order to confirm to what extent each ceramic fragment can get the gDNA of pepper sucked and whether the sucked gDNA can be applied to PCR, the purified CM334 gDNA (1 μg/μL) was used as a material instead of leaves. The purified gDNA in an amount of 1 μL was dropped onto the surface of a plastic petri dish, and the gDNA was sucked into each ceramic fragment, which was used as a template for PCR. As shown in FIG. 2C, as is the case with a positive control group (PC) where 1 μL of CM334 gDNA was used as a template, it was confirmed that PCR products with the same size were amplified in all treated groups. Although there was a little difference in their concentrations the difference was speculated to be due to the difference in size or surface area of the ceramic fragments used therein. Meanwhile, it was confirmed that the ceramic fragments where the gDNA was sucked into can be used as a template for PCR amplification, and thus the possibility whether they can be used for the diagnosis of plant viruses was examined. In order to purify RNAs for negative and positive control using QIAGEN RNeasy Mini Kit, the total RNAs were isolated from sound *Nicotiana rustica* tobacco leaves (for NC) not infected with viruses and *Nicotiana rustica* tobacco leaves (for PC) artificially infected with Tomato spotted wilt virus (TSWV), and used them as templates for reverse transcription. Each of the ceramic fragments was placed on top of TSWV-infected tobacco leaves, pressed with a flat portion on the rear side of metal tweezers to get RNA or virus particles sucked thereinto, and each of the fragments was respectively added into a reverse transcription master premix (ELPIS-Biotech, Korea) already added with 0.5 μL of 10 pmol antisense primer TSNCPR (5'-TCAAGCAAGTTCTGCGAGTT-3': SEQ ID NO: 3), one per each tube. After performing a reverse transcription at 42° C. for 1 hour, 1 μL of the resulting liquid was used as a template for PCR. The PCR premix consisted of 0.5 μL of 10 pmol sense primer (Tsca-F AAACGCCATCAT-TCGTTTTC: SEQ ID NO: 4), 0.5 μL of 10 pmol antisense primer (Tsca-R CATGAAAGTTGACCCGAACA: SEQ ID NO: 5), 4 μL of rTaq-Mix, and 15 μL of DW. The PCR product was denatured at 94° C. for 3 minutes, amplified under the set conditions (94° C./30 sec, 59° C./30 sec, 72° C./60 sec) via 35 amplification cycles, and reacted at 72° C./5 min, and the resultant was electrophoresed on a 1% agarose gel containing EtBr, and the presence/absence of the target PCR product (777 bp) was confirmed. As shown in FIG. 2D, it was confirmed that the expected RT-PCR products were amplified in the ceramic fragments-treated groups except the ceramic fragments 4 and 6. The results suggest that TSWV verification is possible with TSWV RNA or TSWV particles sucked into the ceramic fragments alone, and the higher amplification of PCR product in RT-PCR than gDNA shown in FIG. 2B appears to be due to the higher amount of PCR templates produced by the reverse transcription. From the foregoing, it was suggested that the manufacture of the ceramic fragments into a uniform size and its subsequent use for absorption of biological molecules will enable to obtain a better result.

Example 3. Examination of an Absorption Rate of Biological Molecules According to the Types of Porous Ceramic Cubes of Oxide Material The picture of the surfaces of the respective porous ceramic cube manufactured using the oxide described in Table 1 as a main component enlarged under scanning electron microscope (SEM) is shown in FIG. 3. Since the surface and pore size vary according to the main components of ceramics and their manufacturing temperature, they should be manufactured to obtain the optimum pore size and number of the ceramic cubes in order to improve the absorption rate of the target biological molecules.

TABLE 1

| Sign | Main Component | Manufacturing Temperature (° C.) |
|---|---|---|
| 1 | $Al_2O_3$ | 1450 |
| 2 | $Al_2O_3$ | 1550 |
| 3 | $Fe_2O_3$ | 800 |
| 4 | $Fe_2O_3$ | 850 |
| 5 | $Fe_2O_3$ | 900 |
| 6 | LTCC | 650 |
| 7 | LTCC | 750 |
| 8 | LTCC | 850 |
| 9 | PbO | 1000 |
| 10 | PbO | 1150 |
| 11 | PbO | 1250 |
| 12 | ZnO | 800 |
| 13 | ZnO | 900 |
| 14 | ZnO | 1000 |

Figure 4:
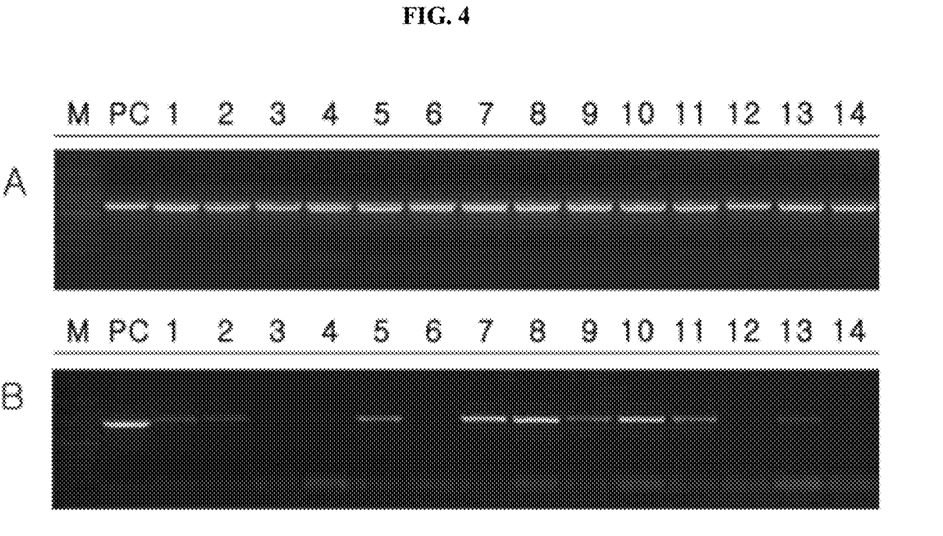
FIG. 4 shows the results of RT-PCR/PCR reactions performed after isolating cucumber mosaic virus (CMV) RNA and genomic DNA isolated from the pepper leaf using the porous ceramic cube prepared using the respective oxide material, wherein A shows the result of RT-PCR performed on the total RNA of CMV; B shows the result of PCR performed on the genomic DNA purified from the pepper leaf, wherein lane M indicates a 1 kb DNA ladder, and lane PC indicates the result wherein, in A, 1 μL of the total RNA isolated from the CMV-infected pepper leaf was used as a template for RT-PCR, and in B, 1 μL of the genomic DNA isolated from CM334 pepper was used as a template.

① Regarding Total RNA Isolated from CMV-Infected *Capsicum annuum* CM334 Pepper Leaves and Genomic DNA Isolated from CM334 Pepper In order to examine the absorption efficiency of biological molecules according to the type of porous ceramic cubes comprised of oxide material, the total RNA isolated from CMV-infected pepper leaves and genomic DNA isolated from CM334 pepper were sucked into each ceramic cube, and used as a template for RT-PCR and PCR, respectively. For CMV, a sense primer (5'-TACATTGAGTCGAGT-CATG-3': SEQ ID NO: 6) and an antisense primer (5'-TGGAATCAGACTGGGACA-3': SEQ ID NO: 7) were respectively added at a concentration of 25 pmol to an RT-PCR premix, and amplified under the set conditions 50° C./20 min, 94° C./10 min, (94° C./30 sec, 55° C./30 sec, 72° C./60 sec) for 35 amplification cycles, 72° C./5 min, and electrophoresed on a 1% agarose gel containing EtBr, and the presence/absence of the target PCR product (670 bp) was confirmed (FIG. 4A). For gDNA, high concentration of gDNA (100 μg) isolated from *Capsicum annuum* CM334 pepper leaves was respectively sucked into each porous ceramic cube, and added one per each PCR tube. The PCR premix consisted of 0.5 μL of 10 pmol sense primer (Tsca-F: AAACGCCATCATTCGTTTTC: SEQ ID NO: 8), 0.5 μL of 10 pmol antisense primer (Tsca-R: CATGAAAGTTGAC-CCGAACA: SEQ ID NO: 9), 4 μL of rTaq-Mix, and 15 μL of DW. The PCR product was denatured at 94° C. for 3 minutes, amplified under the set conditions (94° C./30 sec, 59° C./30 sec, 72° C./60 sec) via 35 amplification cycles, and reacted at 72° C./5 min, and the resultant was electrophoresed on a 1% agarose gel containing EtBr, and the presence/absence of the target PCR product was confirmed. In the case of viral RNA, as shown in 4A, the 14 kinds of ceramic cubes showed similar results (FIG. 4A). In contrast, the efficiency in PCR reaction using the purified gDNA varied according to the cube material and cube manufacturing temperature (FIG. 4B). Lane 1 ($Al_2O_3$, 1450° C.) and Lane 2 ($Al_2O_3$, 1550° C.) showed no significant difference in an amount of amplification, and Lane 3 ($Fe_2O_3$, 800° C.) and Lane 4 ($Fe_2O_3$, 850° C.), which were manufactured at low temperature, showed almost no amplification, however, Lane 5 ($Fe_2O_3$, 900° C.), which was manufactured at high temperature, showed a slight amplification. Lane 6 (LTCC, 650° C.) showed no amplification but Lane 7 (LTCC, 750° C.) and Lane 8 (LTCC, 850° C.) showed a significant level of amplification. Lane 9 (PbO, 1000° C.) and Lane 11 (PbO, 1250° C.) showed a low level of amplification but Lane 10 (PbO, 1150° C.) showed a significant level of amplification. Lane 12 (ZnO, 800° C.) and Lane 14 (ZnO, 1000° C.) showed almost no amplification, but Lane 13 (ZnO, 900° C.) showed a low level of amplification. Conclusively from the above results, genomic DNA absorption rate varied according to cube material and cube manufacturing temperature, and in structures with almost no pores as in Lane 8 (LTCC, 850° C.), Lane 11 (PbO, 1250° C.), and Lane 14 (ZnO, 1000° C.), only a small amount of genomic DNA, which is not detectable under the PCR conditions used in the present invention, was supposed to be sucked.

② Regarding CMV-Infected Pepper Leaves and Purified CMV Particles

In order to examine the absorption efficiency of biological molecules according to the type of the porous ceramic cubes, the CMV-infected pepper leaves and CMV particles were sucked into ceramic cubes and used as templates for RT-PCR and PCR. For CMV, a sense primer (5'-TACATT-GAGTCGAGTCATG-3': SEQ ID NO: 10) and an antisense primer (5'-TGGAATCAGACTGGGACA-3': SEQ ID NO: 11), as a CMV particles-specific primer set, were added respectively at a concentration of 25 pmol to RT-PCR premix (RPampl, Biocubesystem, Korea), and reacted under the conditions of 50° C./20 min, 94° C./10 min, (94° C./30 sec, 55° C./30 sec, 72° C./60 sec) 35 amplification cycles, and 72° C./5 min, and the resultant was electrophoresed on a 1% agarose gel containing EtBr, and the presence/absence of the target PCR product (670 bp) was confirmed. When the purified virus was sucked into a porous ceramic cube there was a higher amplification in the PCR product but the PCR product amplification feature between the two treated sections were similar (FIG. 5).

Figure 5:
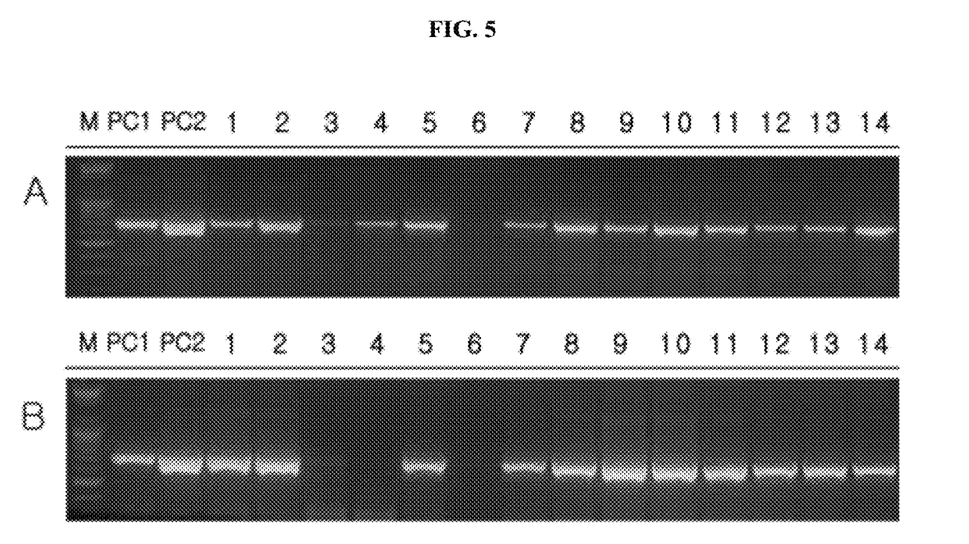
FIG. 5 shows a result of examination on the absorption rate of biological molecules regarding the CMV-infected pepper leaf and purified CMV particles using the porous ceramic cube prepared using the respective oxide material, wherein A indicates CMV-infected pepper leaf, B indicates purified CMV (lane PC1: use 1 μL of the total RNA of the CMV-infected CM334 as a template, and lane PC2: use 1 μL of the total RNA of the CMV-infected *Nicotia tabaccum* Xanthi-nc as a template), and the lanes 1-14 indicate the materials used as shown in Table 1 in that order.

③ Sucking Rate of Biological Molecules According to Manufacturing Temperature and Material of the Porous Ceramic Cube In FIG. 5A, Lanes 1 and 2 have the same main component of $Al_2O_3$, but their manufacturing temperatures are 1450° C. and 1550° C., respectively, and Lanes 3, 4 and 5 have the same main component of $Fe_2O_3$, their manufacturing temperatures are 800° C., 850° C., and 900° C., respectively, and the PCR efficiency was high when DNA was isolated using porous ceramic cubes composed of $Al_2O_3$ and $Fe_2O_3$ manufactured at 1550° C. and 900° C., respectively. Lanes 6, 7, and 8 have the same main component of Low temperature co-fired ceramic (LTCC), and their manufacturing temperatures were 650° C., 750° C., and 850° C., respectively, wherein Lane 6 showed no amplification at all, and Lane 8 showed a higher amplification than Lane 7.

④ Analysis of Pepper DNA Amplification Efficiency Using Porous Ceramic Cubes

A single porous ceramic cube was placed on top of a *Capsicum annuum* sr10 pepper leaf, pressed with a flat portion on the rear side of metal tweezers to get gDNA-sucked thereinto, and the resultant was added into a PCR tube, one per each tube. The solution for PCR reaction was prepared by adding 0.5 μL of 10 pmol sense primer (Primer 10-F: 5'-TGGCTTATCGAAGGAGCCAT-3': SEQ ID NO: 12), 0.5 μL of 10 pmol antisense primer (Primer 10-R: 5'-AGATGAAACCAAAGCCTCCA-3': SEQ ID NO: 13), a cube with gDNA, and 9 μL of DW to 10 μL to a 2×PCR premix (gDamp1, Biocubesystem, Korea), and that for a positive control group was prepared by adding 2 μL of purified gDNA (20 ng/μL) and 7 μL of DW instead of a cube. The PCR product was denatured at 94° C. for 3 minutes, amplified under the set conditions (94° C./30 sec, 58° C./30 sec, 72° C./60 sec) via 35 amplification cycles, and reacted at 72° C./5 min, and the resultant was electrophoresed on a 1% agarose gel containing EtBr, and confirmed whether the PCR product was amplified. As a result, Lane 5 ($Fe_2O_3$, 900° C.), Lane 8 (LTCC, 850° C.), Lane 9 (PbO, 1000° C.), Lane 10 (PbO, 1150° C.) and Lane 14 (ZnO, 1000° C.) showed good amplifications, whereas Lane 6 (LTCC, 650° C.), Lane 7 (LTCC, 750° C.) and Lane 8 (LTCC, 850) and Lane 12 (ZnO, 800° C.), Lane 13 (ZnO, 900° C.) and Lane 14 (ZnO, 1000° C.) were apparently distinguished according to the manufacturing temperature (FIG. 6)

Example 4. LTCC Porous Cubes According to Manufacturing Conditions

① Effect of Manufacturing Temperature of LTCC Porous Cubes on PCR Amplification

Figure 6:
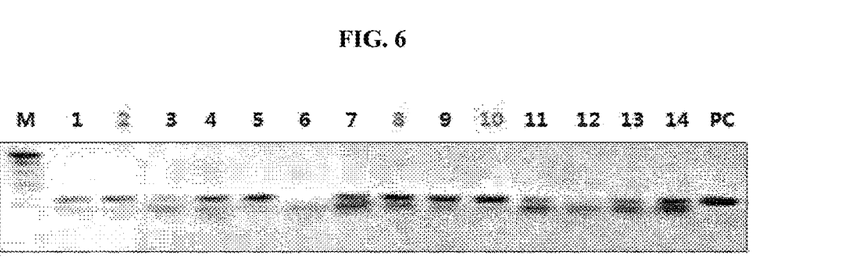
FIG. 6 shows a result of the analysis of DNA amplification efficiency using the various porous ceramic cubes prepared in the present invention with respect to the pepper leaf, wherein lane M indicates a 1 kb DNA ladder, the lanes 1-14 indicate the materials used as shown in Table 1 in that order, and lane PC indicates a result wherein 1 μL of purified gDNA was used as a template.

Upon repeated experiments, there was a distinct difference in gDNA amplification according to manufacturing temperature in LTCC material rather than ZnO (FIG. 6). For detailed examination of the gDNA amplification efficiency according to manufacturing temperature, 5 kinds of LTCC porous cubes (30-34) were newly manufactured. The manufacturing temperature was in the range from 650° C. to 850° C. at 50° C. intervals (30 (LTCC, 650° C.), 31 (LTCC, 700° C.), 32 (LTCC, 750° C.), 33 (LTCC, 800° C.), and 34 (LTCC, 850° C.)). Here, two kinds of primers used are as follows: a sense primer (Primer 10-F: 5'-TGGCTTATC-GAAGGAGCCAT-3': SEQ ID NO: 12), antisense primer (Primer 10-R: 5'-AGATGAAACCAAAGCCTCCA-3': SEQ ID NO: 13) and a sense primer (Primer 146-F: 5'-AGAAGAAAGAGGAGGCTCCA-3': SEQ ID NO: 14), antisense primer (Primer 146-R: 5'-TGGAAGCCTTT-GAGGGATCT-3': SEQ ID NO: 15). The PCR product was denatured at 94° C. for 3 minutes, amplified under the set conditions (94° C./30 sec, 58° C./30 sec, 72° C./60 sec) via 35 amplification cycles, and reacted at 72° C./5 min, and the resultant was electrophoresed on a 1% agarose gel containing EtBr, and confirmed whether the PCR product was amplified. (FIG. 7).

Figure 7:
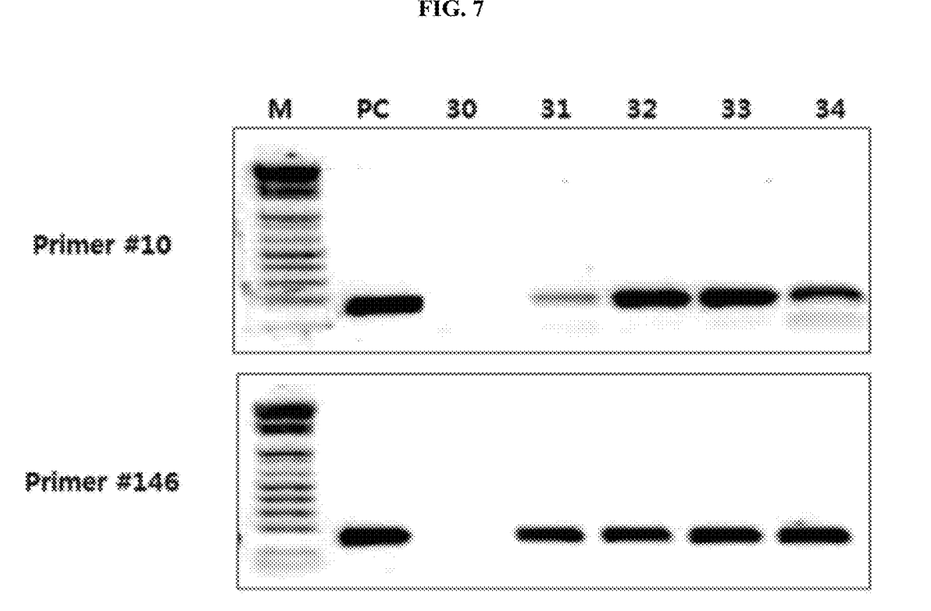
FIG. 7 shows a result of the effect of the temperature for manufacturing Low Temperature Co-fired Cermics (LTCC) porous cube of the present invention on the PCR amplification, wherein lane M indicates a 1 kb DNA ladder, lane PC indicates a result wherein 1 μL of purified genomic DNA (gDNA) was used as a template, and lanes 30-34 are as follows: 30 (LTCC, 650° C.), 31 (LTCC, 700° C.), 32 (LTCC, 750° C.), 33 (LTCC, 800° C.), and 34 (LTCC, 850° C.).

Referring to FIG. 7 showing the PCR results, in the case of Lane 30 (LTCC, 650° C.), there was no gDNA amplification in both kinds of primers as is the case with Lane 6 (LTCC, 650° C.) in FIG. 6. Lane 31 (LTCC, 700° C.) showed a low amplification in primer 10 but showed a high amplification in primer 146. Lane 32 (LTCC, 750° C.) and Lane 33 (LTCC, 800° C.) showed high amplification in both primers. In contrast, Lane 34 (LTCC, 850° C.) showed a similar level of amplification to that of Lane 31 (LTCC, 700° C.), which implies that PCR amplification efficiency may vary according to primers. From the above results, it was confirmed that the suitable temperature for manufacturing porous ceramic cubes with LTCC are in the range from 750° C. to 800° C.

Figure 8:
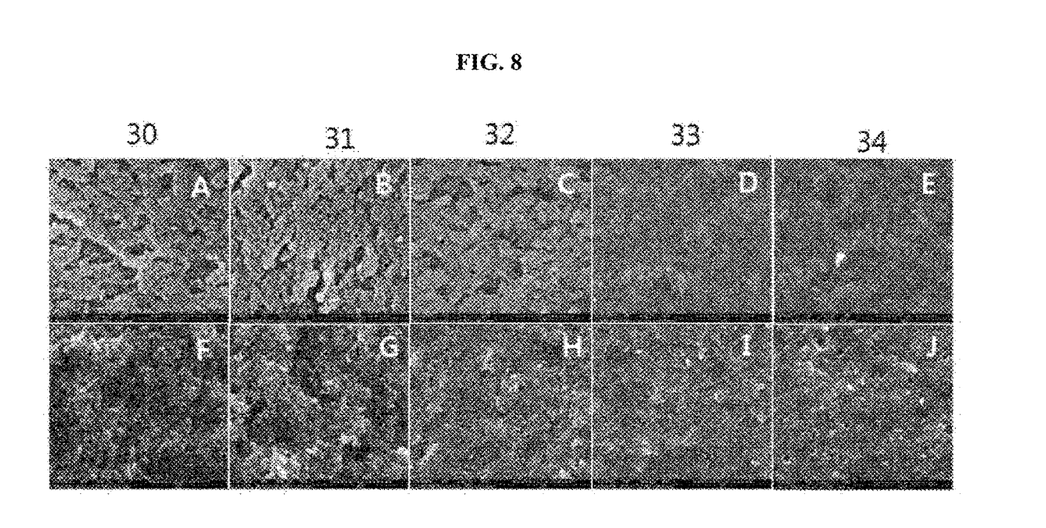
FIG. 8 shows the surface of the LTCC porous ceramic cubes (A-E) and the internal cross-sections (F-J) depending on manufacturing temperature, wherein A-J are pictures observed under 10,000-fold magnification of SEM, and 30-34 are as follows: 30 (LTCC, 650° C.), 31 (LTCC, 700° C.), 32 (LTCC, 750° C.), 33 (LTCC, 800° C.), and 34 (LTCC, 850° C.).

② Surfaces (A-E) and Internal Cross-Sections (F-J) of LTCC Porous Ceramic Cubes According to Manufacturing Temperature In order to examine the characteristics of cubes according to their manufacturing temperature, 5 kinds of LTCC porous ceramic cubes were manufactured and their surfaces (FIGS. 8A-8E) and internal cross-sections (FIGS. 8F-8J), material sucking capacity, and filtration capacity were examined under SEM and TEM, respectively. The surfaces (FIGS. 8A-8E) and internal cross-sections (FIGS. 8F-8J) tended to be smoother as their manufacturing temperature became higher. In both cases, the pore size was similar at the level of µm, and the number of pores tend as the manufacturing temperature tended to be reduced.

③ Analysis of Material Sucking Capacity and Filtrating Capacity of LTCC Porous Cubes According to Manufacturing Temperature The decrease in the number of pores may be understood as the decrease in molecule sucking capacity, but in order to obtain more accurate data, the sucking capacity and filtration capacity were examined using a mixed liquid between artificially manufactured gold nanoparticles (average diameter: 40 nm) and polystylene particles (average diameter: 2 µm, 5 µm, 38-45 µm, Beads & Micro, Korea). 10 cubes manufactured at the same temperature were impregnated per 20 µl, of the above mixed liquid of the two different materials with different diameters, and the filtrate was completely removed using a micropipette and a filter paper. After adding 10 µl, of sterile water to the same tube, the resultant was left at 65° C. for 30 minutes, vortexed for 10 seconds, and the surface characteristics of the remaining cubes and the particle distribution of the washing liquid were observed (5000× under SEM, and 250× under TEM).

Figure 9:
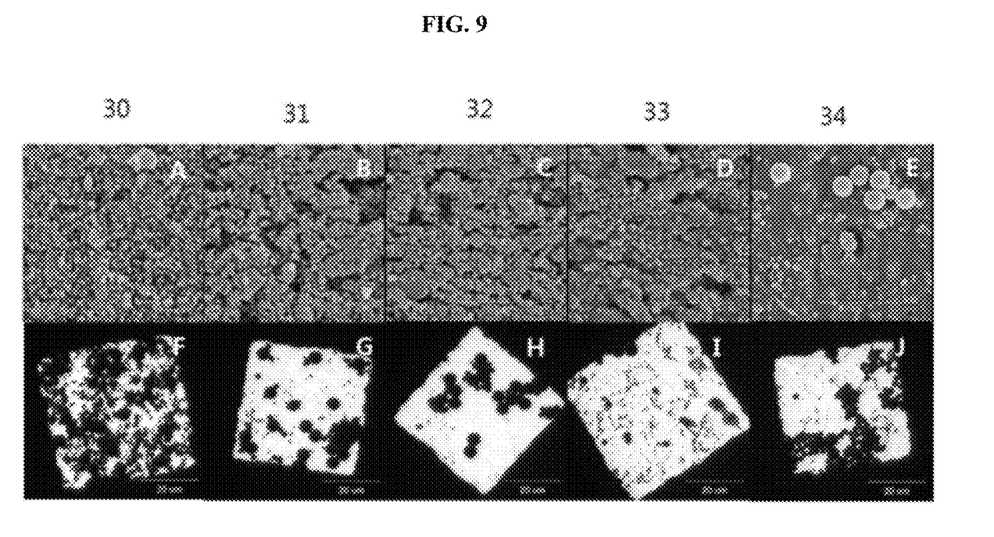
FIG. 9 shows a result of the material absorption capacity and filtration capacity of the LTCC porous ceramic of the present invention according to the manufacturing temperature. The surfaces of cubes (A-E) and the internal cross-sections (F-J) were observed under 5,000-fold magnification of SEM, and 250-fold magnification of TEM, respectively, and the distribution of the mixed solution of gold nanoparticles and polystyrene particles were examined. 30-34 are as follows: 30 (LTCC, 650° C.), 31 (LTCC, 700° C.), 32 (LTCC, 750° C.), 33 (LTCC, 800° C.), and 34 (LTCC, 850° C.).

The observation of the cube surfaces under 5000× revealed that particles with a size similar to that of the pores easily observed in FIGS. 9D and 9E (diameter of about 1 µm or less) were intensively distributed (FIGS. 9D and 9E), and were apparently distinct on the surfaces of cubes 33 and 34. When the cube washing liquid was observed under TEM, the particles with a diameter of 38 µm or higher were rarely observed in all the treated groups (data not provided). The above result appeared to be due to the incomplete removal of the mixed liquid applied on the cube surface. Meanwhile, the particles with a diameter of 2-5 µm were uniformly observed in all the treated groups, and in the treated group of 30 (LTCC, 650° C.), the amount of released particles was significantly higher than in other treated groups (FIG. 9F), and particles with a diameter of about 2 µm were mostly observed in other treated groups (FIGS. 9G-9J). In the cube treated group of 33 (LTCC, 800° C.), particles with a diameter of 2 µm or less were mostly observed being smaller than those in other treated groups.

Figure 10:
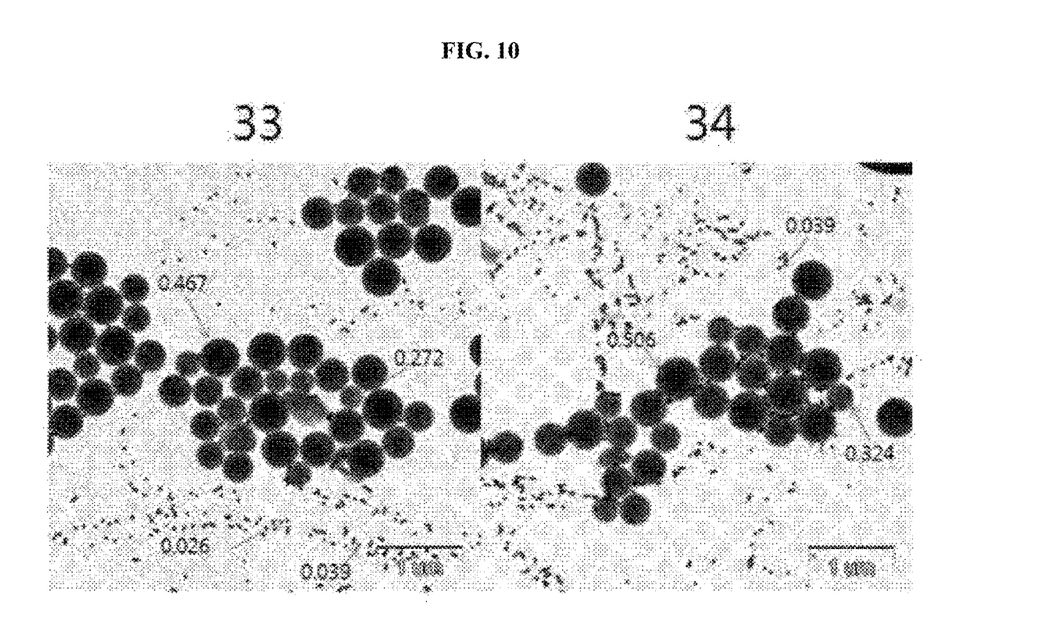
FIG. 10 shows a result of the material absorption capacity and filtration capacity of the LTCC porous ceramic cube of the present invention according to the manufacturing temperature. The distribution of gold nanoparticles and polystyrene particles, after eluting out the gold nanoparticles and polystyrene particles sucked into the interior of the LTCC porous ceramic cubes were examined under 3500-fold magnification of TEM. 33 and 34 are as follows: 33 (LTCC, 800° C.) and 34 (LTCC, 850° C.).

The results shown in FIG. 9 suggest that the synthetic particles are not only passively sucked into the pores by the sucking capacity of the porous ceramic cubes, but also the particles are selectively sucked according to the diameter of the pores. In fact, when the washing liquids of cubes 33 and 34 were observed under high magnification, the pore diameters of the released particles were distributed in a uniform size in the range from 26 nm to 500 nm (FIGS. 10A and 10B). The above result implies that particles with a particular size can be selectively sucked by controlling the pore size.

④ Effect of Cube Surfaces on Amplification Efficiency of PCR Products

The effects of surface roughness and number of pores on the amount of biological molecules sucked (i.e., gDNA) were examined. The surfaces of cube 33 (LTCC, 800° C.) having the best DNA amplification result were abraded for 48 hours and 72 hours, and their surface characteristics and PCR amplification efficiencies were compared.

A single porous ceramic cube was placed on top of a pepper leaf, pressed with a flat portion on the rear side of metal tweezers, and the resultant was added into a PCR tube, one per each tube. The solution for PCR reaction was prepared by adding 0.5 µL of 10 pmol sense primer, 0.5 µL of 10 pmol antisense primer, a cube keeping gDNA, and 9 µL of DW to 10 µL to a 2×PCR premix (gDamp1, Biocubesystem, Korea), and that for a positive control group was prepared by adding 2 µL of purified gDNA (20 ng/µL) and 7 µL of DW instead of a cube. The PCR product was denatured at 94° C. for 3 minutes, amplified under the set conditions (94° C./30 sec, 58° C./30 sec, 72° C./60 sec) via 35 amplification cycles, and reacted at 72° C./5 min, and the resultant was electrophoresed on a 1% agarose gel containing EtBr, and confirmed whether the PCR product was amplified.

Figure 11:
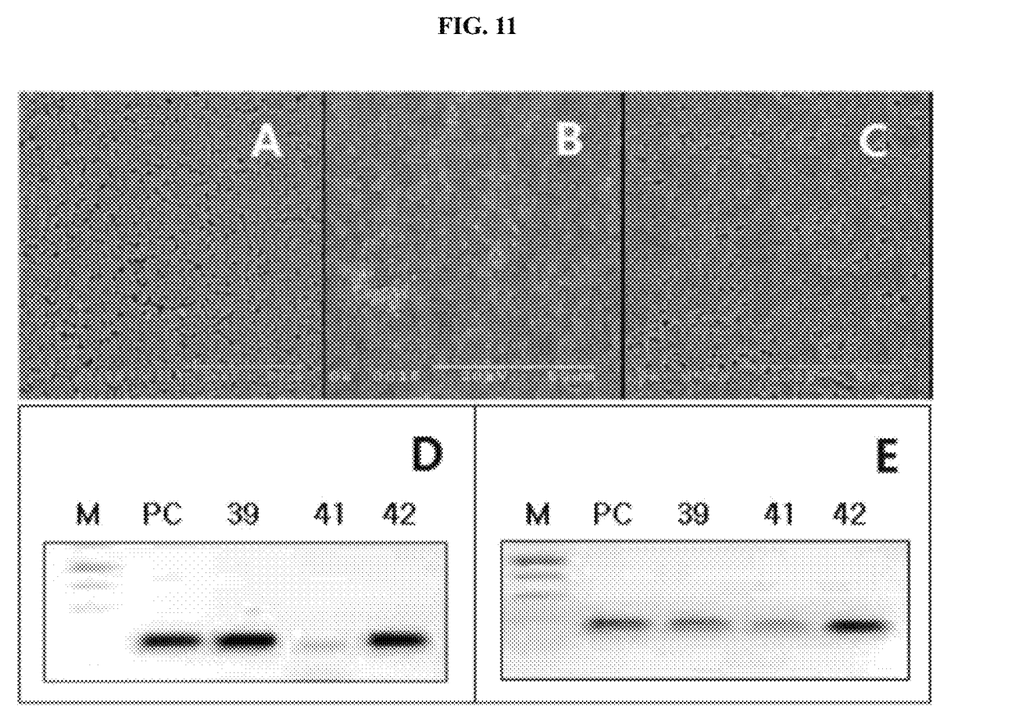

Upon examination of the surface of each cube, the surface roughness was shown to increase in the order of 48 hours, 72 hours, and 0 hour, and the number of pores in the group treated for 48 hours was less than those in other treated groups. The examination of DNA amplification efficiencies of the above samples using primers 10 and 146 for PCR revealed that the PCR amplification efficiency of the group abraded for 48 hours was lower than the groups without abrasion, but the amplification efficiency of PCR product of the group abraded for 72 hours was similar to or slightly higher (FIG. 11).

From the above results, it was confirmed that manufacturing temperature can influence the surface characteristics of cubes in the roughness, area, and pore size. Additionally, it was determined that the change in cube characteristics according to the manufacturing temperature can influence the total sucking amount of reaction inhibitors and a template for PCR in the step of brining a porous solid phase into contact with a biological sample to get the biological molecules present in a biological sample (herein, gDNA or a nucleus) sucked into the pores of the porous solid phase. However, the most important change in the characteristics is that the manufacturing temperature can selectively remove PCR inhibitors by adjusting the number or size and surface areas of pores present in a porous cube, and also have a great influence on obtaining a sufficient amount of the initial template required for PCR.

Example 5. Multiplex RT-PCR Using Biological Molecules Isolated from Multiple-Infected Tobacco Leaves Using an LTCC Cube of the Present Invention

Figure 12:
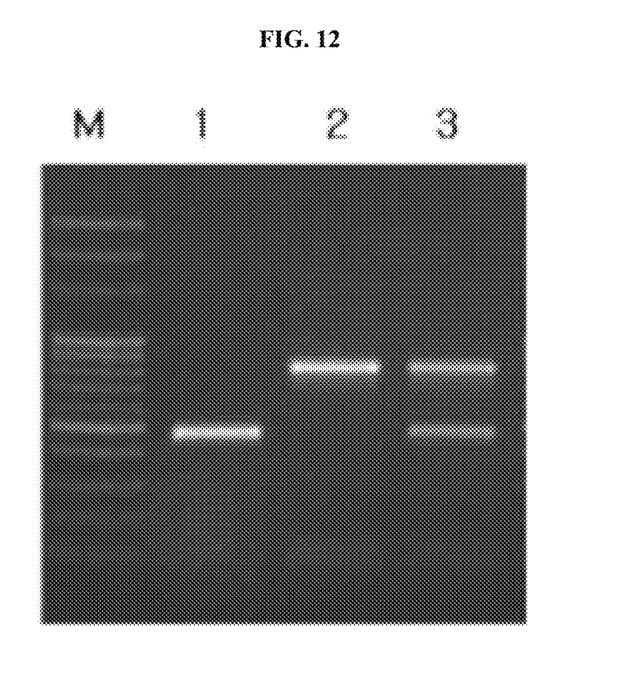
FIG. 12 shows a result of the multiplex RT-PCR using biological molecules isolated from the tobacco leaf as a template and using the LTCC cubes of the present invention, wherein lane M indicates a 1 kb DNA ladder; and lanes 1-3 respectively indicate RT-PCR products of CMV (473 bp), Clover yellow vein virus (CIYVV, 806 bp), CMV (473 bp)+ CIYVV (806 bp).

*N. benthamiana* was subjected to a multiple infection of Cucumber mosaic virus (CMV) and Clover yellow vein potyvirus (ClYVV) and allowed proliferation of the viruses. Then, a single porous ceramic cube (33, LTCC, 800° C.) was placed on top of the multiple-infected tobacco leaf, pressed with a flat portion on the rear side of metal tweezers, and allowed the biological molecules (virus particles or an intermediate form of a virus) to be sucked into a cube. The cube absorbed with a template was added into a tube, one per each tube, and a RT-PCR reaction liquid was dispensed. For the detection of each virus alone, the RT-PCR reaction liquid was prepared by adding 1 µL of 10 pmol sense primer, 1 µL of 10 pmol antisense primer, a cube keeping the template, and 18 µL of DW to a RT-PCR premix (RTamp1, Biocubesystem, Korea). For a multiplex RT-PCR, the solution was prepared by adding the primer for the corresponding virus as described above, and further added with 6 µL of DW. The PCR product was denatured at 94° C. for 3 minutes, amplified under the set conditions (52° C./20 min, 94° C./30 sec, 68° C./30 sec, 72° C./60 sec) via 35 amplification cycles, and reacted at 72° C./5 min, and the resultant was electrophoresed on a 1% agarose gel containing EtBr, and confirmed whether the target PCR product was amplified. The primers used in the RT-PCR for CMV were DPU1 sense primer (5'-CGTCGTGGTTCCCGCTCCG-3': SEQ ID NO: 16) and DPd2 antisense primer (5'-AGCGCGCATCGC-CGAAAGAT-3': SEQ ID NO: 17), and the primers used for ClYVV were 2F sense primer (5'-TAAGA-GAGGGGCACAGTGGA-3': SEQ ID NO: 18) and 2R antisense primer (5'-GCAACAGCACGGGTAACA-3': SEQ ID NO: 19). The result in FIG. 12 suggests that a multiplex RT-PCR can be sufficiently performed using the template sucked into the porous ceramic cube in the above reaction liquid.

Example 6. BAC Plasmid Amplification Using LTCC Cube of the Present Invention in *E. coli*

Figure 13:
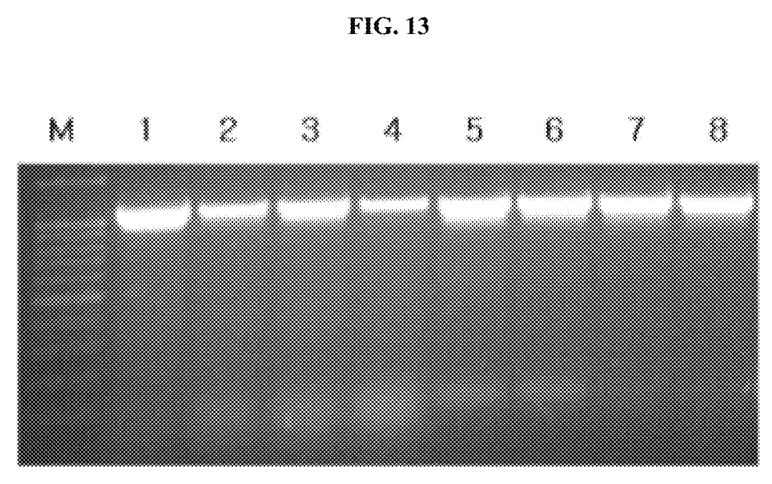
FIG. 13 shows a result of the amplification of BAC plasmid regarding *E. coli* using the LTCC cubes of the present invention, wherein lane M indicates a 1 kb DNA ladder; and lanes 1-4 indicate results wherein 1 μL, 2 μL, 3 μL, and 4 μL of *E. coli* liquid culture were used as a template, respectively, and lanes 5-8 indicate results wherein one, two, three and four porous ceramic cubes (8, LTCC, 850° C.), into which *E. coli* was sucked, were used as a template, respectively. The thickness of PCR bands remained unchanged. That is, *E. coli* was sucked uniformly and the template absorbed into one cube has not distinct difference from that sucked into four cubes. Here, when the primer concentration was increased the PCR band became much thicker when four cubes were used than one cube was used. Lanes 1-4 show the results that the *E. coli* was not uniformly added due to the high viscosity of the *E. coli* liquid culture.

Upon analysis, the porous ceramic cube was suggested to have both absorption capacity and filtration capacity, and the capacities were confirmed by sucking a bacteria culture into a cube and using the resultant as a template for PCR to see whether the PCR was successfully performed. A BAC colony was inoculated using a sterile toothpick into 5 ml of a liquid medium for culturing *E. coli*, and 1 µL, 2 µL, 3 µL, and 4 µl, of *E. coli* culture cultured for 15 hours was used as templates of a positive control. A wrap was laid flat on an experiment bench, aliquoted with 10 µl, of *E. coli* culture thereon, and one, two, three and four porous ceramic cubes (34, LTCC, 850° C.) were added thereto to allow *E. coli* culture to be sucked into the porous ceramic cubes (34, LTCC, 850° C.). The cubes keeping the *E. coli* culture was picked up using metal tweezers, and the liquid remaining on the tweezers was removed using a tissue, and each of the cubes was inserted into a PCR tube and added with a PCR reaction liquid. The PCR reaction liquid was prepared by adding 1 µl, of 10 pmol sense primer (Primer: 5'-GT-CAAATCTGAGGACGCTATGTCT-3': SEQ ID NO: 20), 1 µl, of 10 pmol antisense primer (Primer: 5'-CACTATAGA-GAACTAGGTATGTCGTTG-3': SEQ ID NO: 21), 1-4 cubes keeping template(s), and DW to a final volume of 20 µL, to 10 µl, to a 2×PCR premix (gDamp1, Biocubesystem, Korea). The PCR product was denatured at 95° C. for 3 minutes, amplified under the set conditions (95° C./30 sec, 58° C./30 sec, 72° C./60 sec) via 30 amplification cycles, and reacted at 72° C./10 min, and the resultant was electrophoresed on a 1% agarose gel containing EtBr, and confirmed whether the target PCR product was amplified (FIG. 13). When the culture was directly used as a PCR template the amount of PCR amplification product did not proportionally increase according to the amount of the template added. In contrast, in the group treated with the porous ceramic cube keeping the culture, the amount of PCR amplification product remained constant. The above result suggests that even the template sucked into one porous ceramic cube enabled a sufficient PCR amplification in the reaction liquid described above. Accordingly, the above result implies that the porous ceramic cube can be successfully used for PCR amplification using bacterial as a template.

Figure 14:
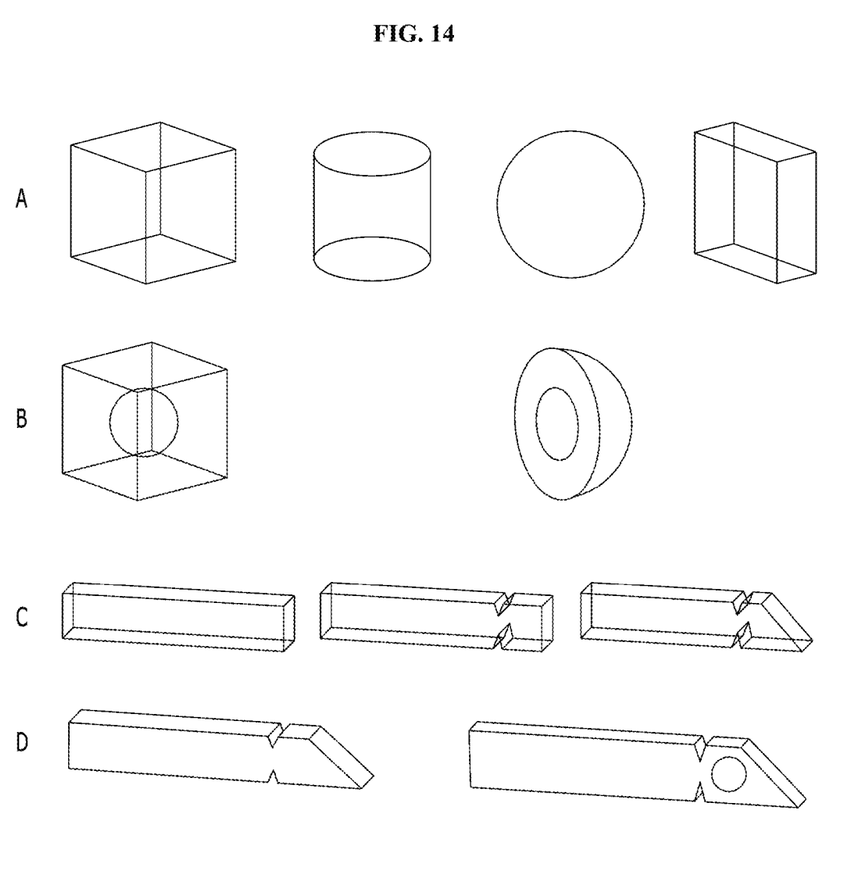
FIG. 14 shows a result of the type of usable porous ceramics for sucking biological molecules, wherein A indicates a single simple structure (square, circle, etc.); B indicates a structure with a hole-shaped space inside the single simple structure; C indicates a complex structure wherein various surface pore size and materials are combined therein; and D indicates a double structure with different density (left) and a structure with pores inside (right).

Example 7. Types of Usable Porous Ceramics for Absorption of Biological Molecules In the present invention, according to the purposes, a structure such as that shown in FIG. 14 may be usable for the efficient absorption of biological molecules from a biological sample. As a basic structure, a cube, a cylinder, a sphere or a cuboid may be possible (FIG. 14A), and a type with a large pore space may be possible for increasing absorption capacity (FIG. 14B). In the structure of FIG. 14A, a genetic material is selectively sucked only through the surface of pores, whereas the structure of FIG. 14B is a structure to increase the amount of the genetic material to be sucked by increasing the sucking rate. This requires a uniform pore size on the external wall of a hole, and the function of the hole is to increase the absorption capacity and simultaneously reduces a PCR step by adding a PCR primer in advance. This is suitable later for genomic DNA PCR which requires a large amount of the initial template.

Additionally, the structures shown in the middle and on the right of FIG. 14C are structures, in which the area on the right with a dent, into which biological molecules are kept, is designed so that, upon a slight pressure thereon, the area is detached and easily fall down into a PCR tube, and, because the size of the cube is too small, part of the dent area was cut out so that the front end of a rod can be easily cut off to the extent of 1 mm$^3$ in the case of a cubical structure usable in the manufacture of real products, and the rear area of the rod is the site where the plastic rod manufactured as a hand knob is inserted. The structure with a sharp end shown in FIG. 14D is a structure for easy piercing when seeds or plants are used. Since the genetic material can be introduced into the entire rod when the rod is made of the same material, design variations can be possible by varying the materials so that the absorption capacity can be improved and also the genetic material can be collected into the front end, which is to be inserted into a PCR tube, and is also very effective in preventing contamination and improving absorption capacity.

What is claimed is:
1. A method for rapidly isolating a biological molecule for a nucleic acid amplification reaction from a biological sample, the method comprising:
physically contacting a cubical shaped-porous solid phase having a plurality of pores varied in size with a biological sample;
physically sucking the biological molecule present in the biological sample into the plurality of pores of the cubical shaped-porous solid phase to prepare a polymerase chain reaction (PCR) template,
wherein the cubical shaped-porous solid phase is made of ceramic having oxide material, which is selected from the group consisting of Al2O3, Fe2O3, low temperature co-fired ceramic (LTCC), PbO, and ZnO, wherein,
the Al2O3, has a temperature of 1450° C.-1550° C.,
the Fe2O3 has a temperature of 850° C.-900° C.,
the LTCC has a temperature of 750° C.-850° C.,
the PbO has a temperature of 1000° C.-1250° C., and
the ZnO has a temperature of 900° C.-1000° C.;
adding the PCR template into a tube for a PCR; and isolating the biological molecule for the nucleic acid amplification reaction from the biological sample without using a chemical buffer which reacts to the biological molecule.

2. The method of claim 1, wherein the biological sample is derived from an animal, a plant, a bacterium, or a fungus.

3. The method of claim 1, wherein the biological molecule is DNA, RNA, dsRNA, microRNA, viroid, virus, bacteria, fungi or microalgae.

4. The method of claim 1, wherein the porous solid phase is in the shape of a cube, a cuboid, a sphere, a cylinder, a bar, a bar with a dent at one end or a bar with a sharp end.

* * * * *